(12) United States Patent
Sorensen et al.

(10) Patent No.: US 8,939,927 B2
(45) Date of Patent: Jan. 27, 2015

(54) SYSTEMS AND METHODS FOR SMALL BORE ASPIRATION

(75) Inventors: Gary P. Sorensen, Laguna Niguel, CA (US); Eric Lee, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 161 days.

(21) Appl. No.: 13/323,176

(22) Filed: Dec. 12, 2011

(65) Prior Publication Data

US 2012/0157912 A1    Jun. 21, 2012

Related U.S. Application Data

(60) Provisional application No. 61/423,752, filed on Dec. 16, 2010.

(51) Int. Cl.
| A61M 1/00 | (2006.01) |
| A61B 17/20 | (2006.01) |
| A61F 9/007 | (2006.01) |
| A61F 9/00 | (2006.01) |
| A61B 18/18 | (2006.01) |

(52) U.S. Cl.
CPC .......... *A61F 9/00745* (2013.01); *A61M 1/0058* (2013.01); *A61F 9/00763* (2013.01)
USPC ............... 604/35; 604/22; 604/28; 604/30; 606/6; 606/107

(58) Field of Classification Search
USPC ................. 604/22, 30–35, 43; 606/4–6, 107
See application file for complete search history.

(56) References Cited

U.S. PATENT DOCUMENTS

| 2,295,840 | A | 9/1942 | Grint |
| 3,589,363 | A | 6/1971 | Banko |
| 3,884,238 | A | 5/1975 | O'Malley et al. |
| 4,019,514 | A | 4/1977 | Banko et al. |
| 4,031,896 | A | 6/1977 | Ronnmark |
| 4,117,843 | A | 10/1978 | Banko et al. |
| 4,324,243 | A | 4/1982 | Helfgott et al. |

(Continued)

FOREIGN PATENT DOCUMENTS

| AU | 200151298 B2 | 11/2005 |
| DE | 102007031722 A | 1/2009 |

(Continued)

OTHER PUBLICATIONS

International Searching Authority, International Search Report, PCT/US2011/064423, Apr. 4, 2012, 2 pages.

(Continued)

*Primary Examiner* — Nicholas Lucchesi
*Assistant Examiner* — Leah Stohr

(57) ABSTRACT

An assembly for a phacoemulsification surgical system includes an aspiration system arranged to aspirate fluid from a surgical site. The aspiration system includes an aspiration path within the phacoemulsification hand piece and includes a flexible small bore aspiration tubing in fluid communication with the aspiration path. The small bore aspiration tubing has a nominal inner diameter smaller than about 0.050 inch to reduce levels of occlusion surge within the surgical system. A high-output, peristaltic pump communicates with the small bore aspiration tubing and is operable to create a flow through the small bore aspiration tubing.

15 Claims, 6 Drawing Sheets

(56) References Cited

U.S. PATENT DOCUMENTS

| | | | |
|---|---|---|---|
| 4,418,944 A | 12/1983 | Haines et al. | |
| 4,921,477 A * | 5/1990 | Davis | 604/22 |
| 4,935,005 A | 6/1990 | Haines | |
| 5,041,096 A | 8/1991 | Beauchat et al. | |
| 5,364,342 A | 11/1994 | Beauchat et al. | |
| 5,437,678 A | 8/1995 | Sorensen | |
| 5,499,969 A | 3/1996 | Beauchat et al. | |
| 5,585,011 A | 12/1996 | Saaski et al. | |
| 5,651,783 A * | 7/1997 | Reynard | 606/4 |
| 5,928,203 A | 7/1999 | Davey et al. | |
| 6,059,544 A | 5/2000 | Jung | |
| 6,149,633 A | 11/2000 | Maaskamp | |
| 6,261,283 B1 | 7/2001 | Morgan et al. | |
| 6,273,878 B1 | 8/2001 | Muni | |
| 6,273,894 B1 | 8/2001 | Dykes | |
| 6,293,926 B1 | 9/2001 | Sorensen | |
| 6,402,206 B1 | 6/2002 | Simmons et al. | |
| 6,436,077 B1 | 8/2002 | Davey et al. | |
| 6,478,781 B1 | 11/2002 | Urich et al. | |
| 6,572,349 B2 | 6/2003 | Sorensen et al. | |
| 6,601,879 B2 | 8/2003 | Donoho et al. | |
| 6,632,214 B2 | 10/2003 | Morgan et al. | |
| 6,719,011 B2 | 4/2004 | Cull et al. | |
| 6,740,074 B2 | 5/2004 | Morgan et al. | |
| 6,752,795 B2 | 6/2004 | Cull | |
| 6,902,542 B2 | 6/2005 | Gordon | |
| 6,908,451 B2 | 6/2005 | Brody et al. | |
| 6,962,488 B2 | 11/2005 | Davis et al. | |
| 7,083,591 B2 | 8/2006 | Cionni | |
| 7,217,257 B2 | 5/2007 | Cull et al. | |
| 7,393,189 B2 | 7/2008 | Davis et al. | |
| 7,727,179 B2 | 6/2010 | Barrett | |
| 7,914,482 B2 | 3/2011 | Urich et al. | |
| 7,981,074 B2 | 7/2011 | Davis et al. | |
| 8,092,427 B2 | 1/2012 | Urich et al. | |
| 8,303,553 B2 | 11/2012 | Kuebler et al. | |
| 8,398,582 B2 | 3/2013 | Gordon et al. | |
| 2002/0022810 A1 | 2/2002 | Urich | |
| 2002/0128560 A1 | 9/2002 | Urich | |
| 2003/0236508 A1 | 12/2003 | Cull | |
| 2004/0039351 A1 | 2/2004 | Barrett | |
| 2005/0113741 A1 | 5/2005 | Huang et al. | |
| 2006/0058728 A1 | 3/2006 | Urich | |
| 2006/0058729 A1 * | 3/2006 | Urich | 604/22 |
| 2006/0078448 A1 | 4/2006 | Holden | |
| 2006/0084937 A1 | 4/2006 | Akahoshi | |
| 2006/0100570 A1 | 5/2006 | Urich et al. | |
| 2006/0173404 A1 | 8/2006 | Urich et al. | |
| 2006/0173426 A1 | 8/2006 | Urich et al. | |
| 2006/0224163 A1 * | 10/2006 | Sutton | 606/107 |
| 2006/0253062 A1 | 11/2006 | Liao et al. | |
| 2007/0106211 A1 | 5/2007 | Provost-tine et al. | |
| 2007/0179438 A1 | 8/2007 | Morgan | |
| 2008/0167595 A1 | 7/2008 | Porter et al. | |
| 2008/0188792 A1 | 8/2008 | Barrett | |
| 2008/0312594 A1 | 12/2008 | Urich | |
| 2010/0130944 A1 | 5/2010 | Music | |
| 2010/0152685 A1 | 6/2010 | Goh | |
| 2010/0286651 A1 | 11/2010 | Sorensen | |
| 2010/0305496 A1 | 12/2010 | Kuebler et al. | |
| 2010/0312170 A1 | 12/2010 | Maaskamp et al. | |
| 2012/0157912 A1 | 6/2012 | Sorensen et al. | |
| 2012/0157943 A1 | 6/2012 | Sorensen et al. | |

FOREIGN PATENT DOCUMENTS

| | | |
|---|---|---|
| WO | 01/76681 A1 | 10/2001 |
| WO | 02/19896 A2 | 3/2002 |
| WO | 02/019896 A3 | 8/2002 |
| WO | 03/030717 A2 | 4/2003 |
| WO | 03/030717 A3 | 3/2004 |
| WO | 2004/030725 A1 | 4/2004 |
| WO | 2007/075200 A1 | 7/2007 |
| WO | 2009/007223 A1 | 1/2009 |
| WO | 2009/076717 A1 | 6/2009 |
| WO | 2012/082623 A1 | 6/2012 |

OTHER PUBLICATIONS

International Searching Authority, Written Opinion of the International Searching Authority, PCT/US2011/064423, Apr. 4, 2012, 7 pages.

Flared Peristaltic Pump Tubing—ICM MS Pump Tubing—Santoprene® Tubing—Flared End Peristaltic Tubing; FlaredTubing.com (Copyright 2009) (3 pages) (see file "Flaredtubing_com").

Hausermans abstract from Ophthalmologia Belgica "Breaking the link between vacuum and aspiration flow" (2006).

Stellaris™ sales brochure "StableChamber_Pack" (Copyright 2007).

Krieglstein, G.K., et al. (R.N. Weinreb, Douglas D. Koch, and Thomas Kohnen) "Cataract and Refractive Surgery: Progress III"; Essentials in Ophthalmology; published 2009 (Google book search screen images).

European Patent Office, Extended European Search Report, Application No. 11849053.1, Publication No. 2651354, Jul. 1, 2014, 7 pages.

* cited by examiner

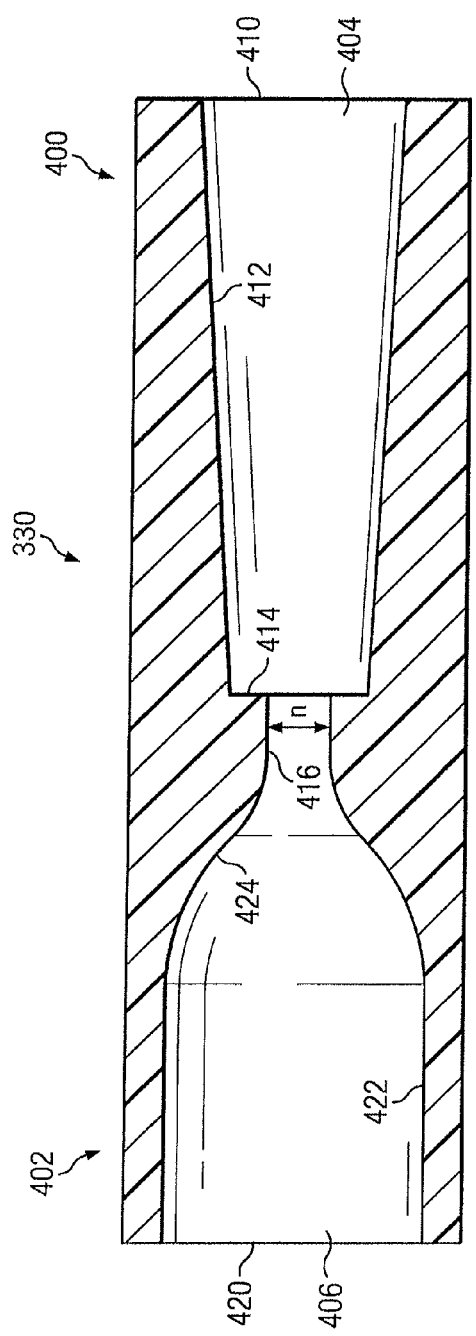
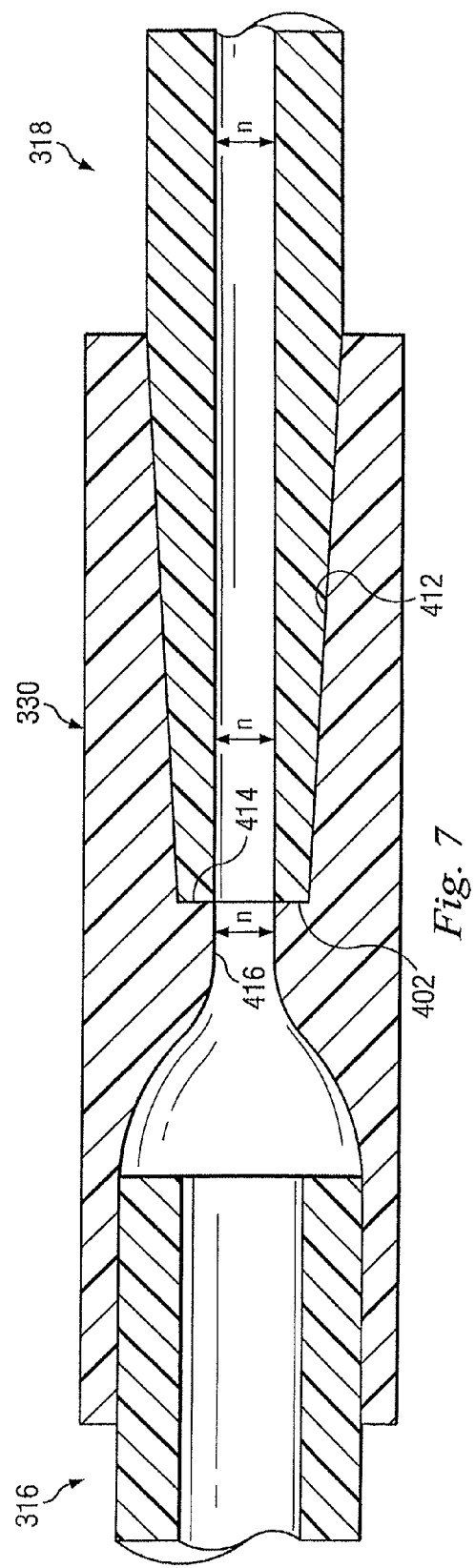

SYSTEMS AND METHODS FOR SMALL BORE ASPIRATION

PRIORITY CLAIM

This application claims the benefit of priority of U.S. Provisional Patent Application Ser. No. 61/423,752 titled "Small Bore Aspiration System", filed on Dec. 16, 2010, whose inventors are Gary P. Sorensen and Eric Lee.

BACKGROUND OF THE INVENTION

The present invention relates to aspiration systems used in phacoemulsification procedures, and more particularly, to aspirations systems employing small bore elements to improve operation.

Typical surgical instruments suitable for phacoemulsification procedures on cataractous lenses include an ultrasonically driven phacoemulsification hand piece with a cutting needle and an irrigation sleeve, and a control console. The hand piece is attached to the control console by an electric cable and flexible tubing. The flexible tubing supplies irrigation fluid to the surgical site and carries aspiration fluid from the surgical site to a waste or discard reservoir.

During a phacoemulsification procedure, the tip of the cutting needle and the end of the irrigation sleeve are inserted into the anterior segment of the eye through a small incision in the eye's outer tissue. The surgeon brings the tip of the cutting needle into contact with the lens of the eye, so that the vibrating tip fragments the lens. The resulting fragments are aspirated out of the eye through the interior bore of the cutting needle, along with irrigation fluid provided to the eye during the procedure.

Throughout the procedure, irrigating fluid is infused into the eye, passing between the irrigation sleeve and the cutting needle and exiting into the eye at the tip of the irrigation sleeve and/or from one or more ports or openings formed into the irrigation sleeve near its end. This irrigating fluid prevents the collapse of the eye during the removal of the emulsified lens, protects the eye tissue from the heat generated by the vibrating of the ultrasonic cutting needle, and suspends the fragments of the emulsified lens for aspiration from the eye.

During the surgical procedure, the console controls irrigation flow rates and aspiration flow rates to maintain a proper intra-ocular chamber balance in an effort to maintain a relatively consistent fluid pressure at the surgical site in the eye.

Aspiration flow rates of fluid from the eye are typically regulated by an aspiration pump that creates a vacuum in the aspiration line. The aspiration flow and/or vacuum are set to achieve the desired working effect for the lens removal. While a consistent fluid pressure in the eye is desirable during the phacoemulsification procedure, common occurrences or complications create fluctuations or abrupt changes in fluid flow and pressure at the eye. One known cause for these is occlusions or flow obstructions that block the needle tip. This common, and sometimes desirable occurrence, results in a sharp increase in vacuum in the aspirating line. When the occlusion is removed, the resulting high demand for fluid from the eye to relieve the vacuum can cause a sudden shallowing of the anterior chamber, as the aspiration flow momentarily sharply increases over the irrigation flow.

The degree of shallowing in the eye is a function of vacuum level within the aspiration path when the occlusion breaks, as well as resistive and compliance characteristics of the fluid path. Increased resistance in the aspiration path reduces the flow rate associated with occlusion break and thereby lessens the pressure drop from the irrigating source to the eye and the resulting shallowing of the anterior chamber.

The problem of occlusion surge has been addressed in the past in a number of ways. One method includes adding a reduced cross-sectional orifice to create a barrier reducing flow. While such a reduced area reduces the effects of occlusion surge, reduction of aspiration path cross-section can also increase the potential for clogging during the procedure. Other methods have been used or proposed that involve torturous paths, with corners, angles, and fluid restrictors that are also subject to clogging. Some prior solutions involve a resistive element at or near the pump. However, the effectiveness of these solutions is limited due to the relatively large tubing compliance between the resistive element and the eye. Another attempted solution has been the use of increased lengths of flexible aspiration tubing in an attempt to increase overall tubing resistance. This solution of adding flexible tubing length has the undesirable effect of adding additional compliance to the aspiration path. The additional compliance increases the demand for fluid from the eye during occlusion break, sometimes entirely offsetting the benefits obtained by the longer tubing length.

Methods with small bore aspiration lines, such as lines with a diameter of 0.050 inches or less, have generally been avoided because small bore lines may become easily clogged, potentially creating inconsistent flow rates, resulting in high levels of occlusion surge, and possibly resulting in undesirable levels of trauma during the surgical procedure. In addition, methods with small bore aspiration lines have generally been avoided because, as a result of the small bore with increased wall resistance, pumping that achieves a desirable flow rate can be difficult.

SUMMARY OF THE INVENTION

In one exemplary aspect, the present disclosure is directed to an assembly for a phacoemulsification surgical system. The assembly includes a phacoemulsification hand piece configured to deliver irrigating fluid to a surgical site. The phacoemulsification hand piece includes an ultrasonic tip having a lumen sized and configured to aspirate aspirating fluid from the surgical site. The assembly also includes an irrigation system arranged to provide the irrigating fluid to the phacoemulsification hand piece to irrigate the surgical site and includes an aspiration system arranged to aspirate the aspirating fluid from the surgical site. The aspiration system includes an aspiration path within the phacoemulsification hand piece. The aspiration path extends from the ultrasonic tip and is arranged and configured to permit flow of the aspirating fluid through the hand piece. The aspiration system also includes a flexible small bore aspiration tubing in fluid communication with the aspiration path. The small bore aspiration tubing has a nominal inner diameter smaller than about 0.050 inch (other diameters are also contemplated) to reduce levels of occlusion surge within the surgical system. The inner diameter is substantially consistent through the length of the small bore aspiration tubing. A high-output, peristaltic pump communicates with the small bore aspiration tubing and is operable to create a flow of about 60 cc/min. through the small bore aspiration tubing.

In some aspects, the small bore aspiration tubing includes a flared portion on the inner diameter of at least one end, wherein when in an unloaded condition, the flared portion has an inner diameter larger than the nominal inner diameter of the small bore aspiration tubing. In additional aspects, the assembly includes a connector configured to receive at least a portion of the flared portion of the small bore aspiration tubing. The connector may be sized to apply radial compression on the flared portion when the flared portion is inserted in the connector such that when the small bore aspiration tubing is disposed within the connector, the inner diameter of the flared portion is about the same diameter as the neck and the nominal diameter of the small bore aspiration tubing.

In another exemplary aspect, the present disclosure is directed to a small bore aspiration system arranged to receive aspiration fluid from an ultrasonic tip used in a phacoemulsification surgical assembly. The system includes an aspiration path within the phacoemulsification hand piece that extends from the ultrasonic tip and is arranged and configured to permit flow of the aspirating fluid through the hand piece. It also includes a flexible small bore aspiration tubing in fluid communication with the aspiration path. The small bore aspiration tubing has a nominal inner diameter smaller than about 0.050 inch (other diameters are also contemplated) to reduce levels of occlusion surge within the surgical system, and the inner diameter being substantially consistent through the length of the small bore aspiration tubing. The system also includes a high-output, peristaltic pump in communication with the small bore aspiration tubing.

In yet another exemplary aspect, the present disclosure is directed to a method for aspirating a surgical site with an aspiration system of a phacoemulsification surgical system. The method includes the steps of creating a vacuum in an aspiration system of a phacoemulsification system, directing fluid through a needle of the phacoemulsification hand piece, and directing fluid through an aspiration passage within the hand piece having a size ratio between the aspiration passage bore inner diameter and the needle bore inner diameter of less than about 1.5 (or, for example, 1.3). The method also includes directing fluid through a small bore flexible aspiration tubing extending from the hand piece to a fluid cassette. The small bore flexible aspiration tubing has a substantially consistent nominal diameter across its length that is less than about 0.050 inch (other diameters are also contemplated). In some embodiments, the size ratio between the small bore flexible aspiration tubing inner diameter and the needle bore inner diameter is less than about 1.5 (or, for example, 1.3). The method also includes directing fluid into a cassette and a pump configured to create a vacuum in the aspiration system.

It is to be understood that both the foregoing general description and the following detailed description are exemplary and explanatory only and are intended to provide further explanation of the invention as claimed. The following description, as well as the practice of the invention, sets forth and suggests additional advantages and purposes of the invention.

BRIEF DESCRIPTION OF THE DRAWINGS

The accompanying drawings, which are incorporated in and constitute a part of this specification, illustrate several embodiments.

FIG. 6 is an illustration of a cross-sectional view of a connector usable to connect the flexible tubing in FIGS. 4 and 5 to additional aspiration components of the fluidics system in FIG. 3 according to one aspect of the present disclosure.

FIG. 7 is an illustration of a cross-sectional view of the connector of FIG. 6 with the end portion of FIG. 5 of the flexible tubing according to one aspect of the present disclosure.

DETAILED DESCRIPTION OF SEVERAL EMBODIMENTS

Reference is now made in detail to several exemplary embodiments, examples of which are illustrated in the accompanying drawings. Wherever possible, the same reference numbers are used throughout the drawings to refer to the same or like parts.

This disclosure is directed to an aspiration system that may achieve lower levels of occlusion surge than currently known systems under similar conditions. These lower levels derive from a novel, small bore aspiration line that provides increased fluid resistance when compared to known systems. This increased fluid resistance dampens or reduces the levels of occlusion surge in the aspiration line, potentially resulting in more stable and predictable surgical processes.

The small bore aspiration tubing decreases occlusion surge levels in at least two ways. First, the smaller diameter of the small bore fluid path introduces a greater level of wall resistance than larger bore fluid paths. This wall resistance decreases the amount of flow variation over short periods of time, rendering the flow more consistent, with lower levels and more controlled surge when surges occur. Second, the small bore aspiration tubing, due to its smaller surface area than larger bore aspiration tubes, is subject to less compliant deformation (radial collapse) as a result of high vacuum levels within the tube, as may occur when aspiration flow is limited or blocked by an occlusion.

As indicated above, however, small bore aspiration tubing has generally been considered easily clogged. Therefore, small bore aspiration tubing having a diameter of less than about 0.050 inch have not typically been used in aspiration lines. However, the small bore aspiration tubing disclosed herein may achieve suitable, consistent flow rates with reduced clogging by using consistent-flow junction components and suitable relative dimensions between components. Thus, small bore aspiration tubing can be used, with acceptable flow tendencies, to decrease the level of occlusion surges and provide more control during surgical procedures.

Figure 1:
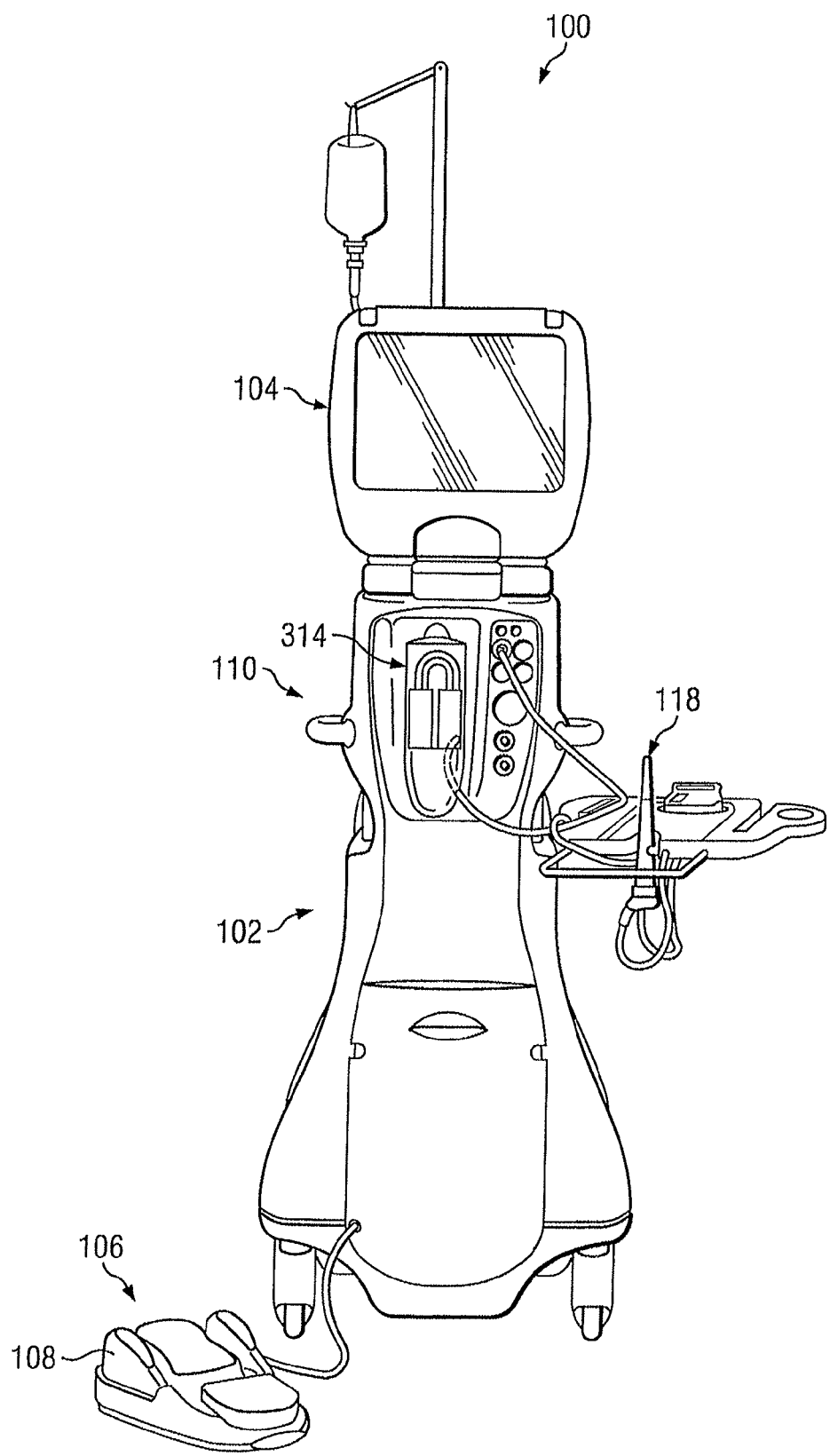
FIG. 1 is an illustration of an exemplary phacoemulsification surgical console according to an embodiment implementing the teachings and principles described herein.
Figure 2:
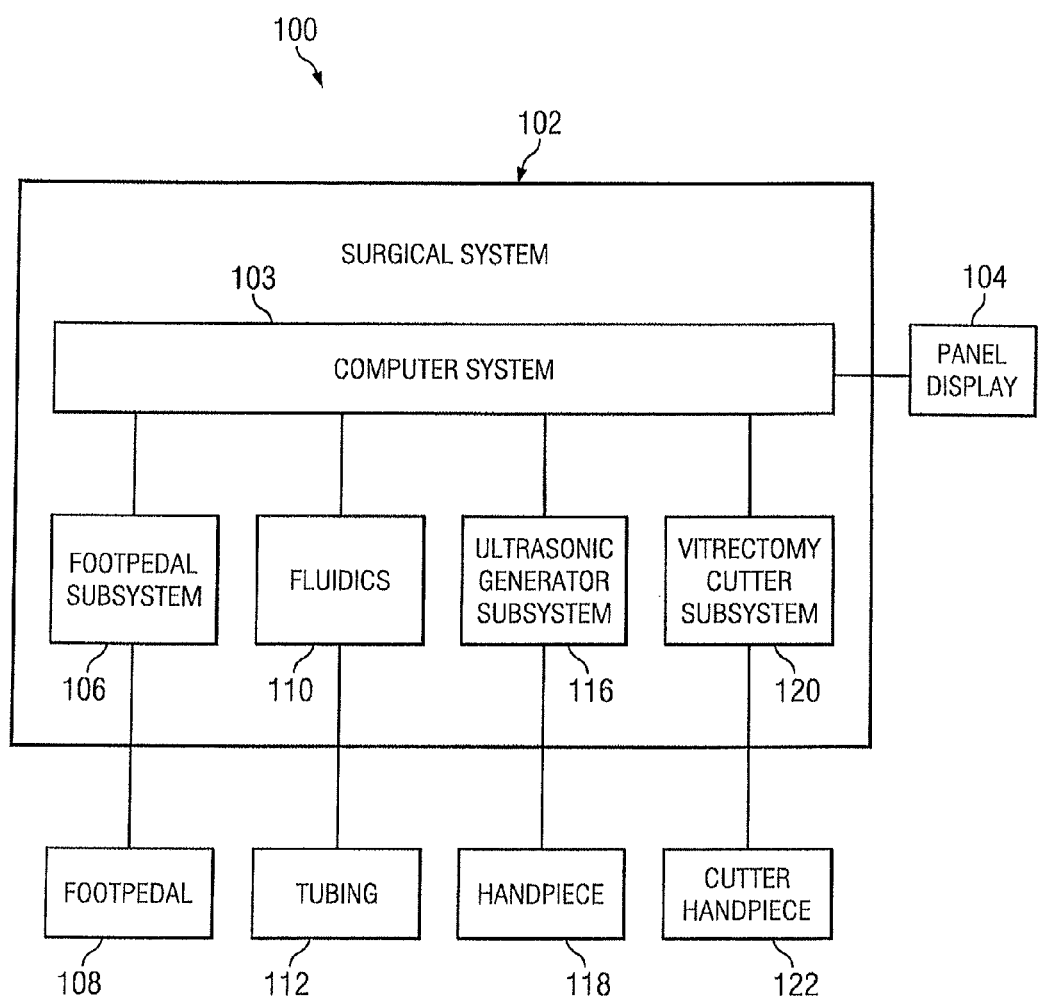
FIG. 2 is a block diagram of the phacoemulsification console of FIG. 1 showing various subsystems including a fluidics subsystem that drives aspiration according to the principles of the present disclosure.

FIG. 1 illustrates an exemplary emulsification surgical console, generally designated 100. FIG. 2 is a block diagram of the console 100 showing various subsystems that operate to perform a phacoemulsification procedure. The console 100 includes a base housing 102 with a computer unit 103 and an associated display screen 104 showing data relating to system operation and performance during an emulsification surgical procedure. The console 100 also includes a number of subsystems that are used together to perform an emulsification surgical procedure. For example, the subsystems include a foot pedal subsystem 106 including, for example, a foot pedal 108, a fluidics subsystem 110 including an irrigation system and an aspiration system that deliver fluid to and aspirate fluid from the eye through flexible tubing 112, an ultrasonic generator subsystem 116 including an ultrasonic oscillation hand piece 118 with a cutting needle, and a pneumatic vitrectomy cutter subsystem 120 including a vitrectomy hand piece 122. These subsystems overlap and cooperate to perform various aspects of the procedure.

Figure 3:
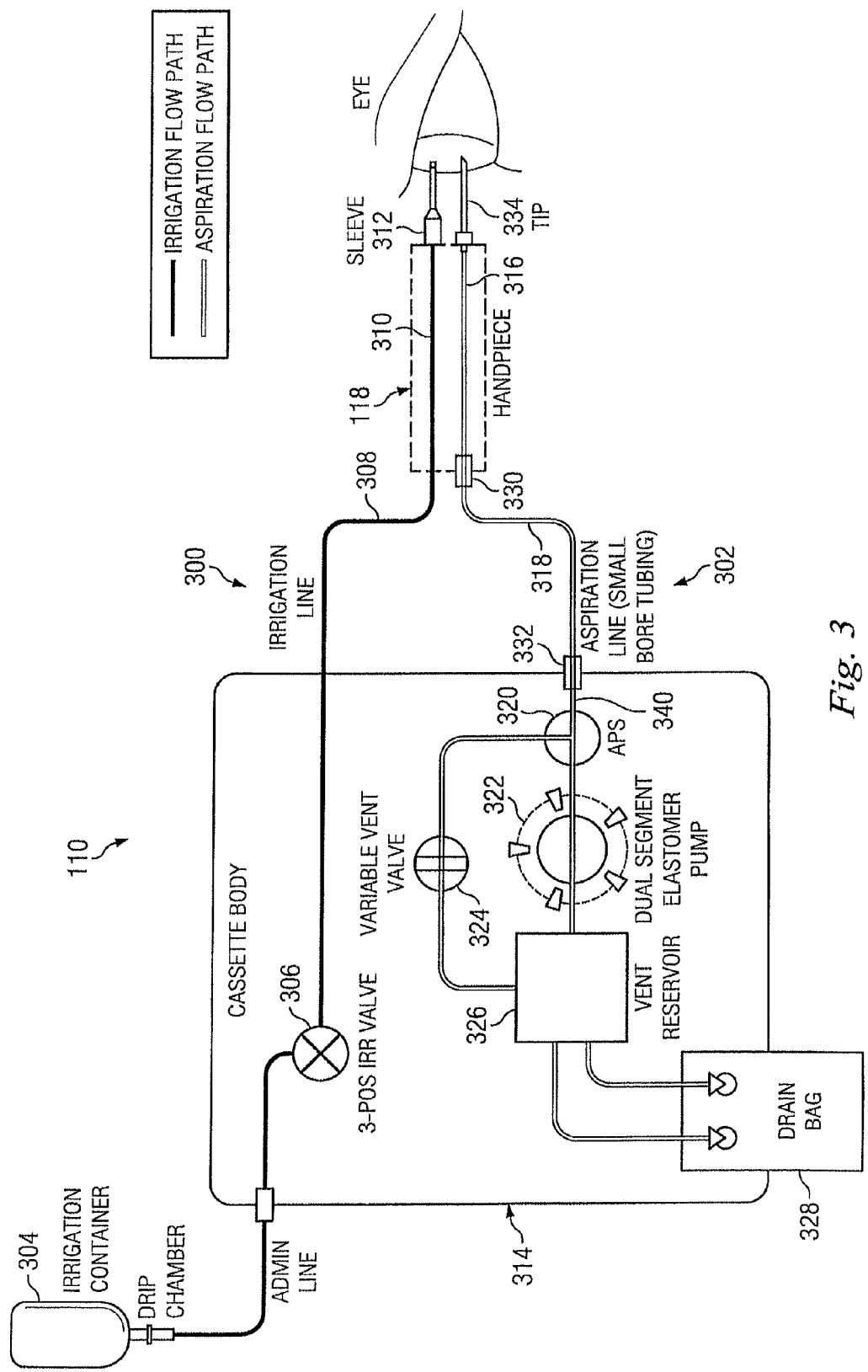
FIG. 3 is a schematic of an exemplary fluidics subsystem usable with the phacoemulsification surgical console of FIGS. 1 and 2, according to an embodiment.

FIG. 3 illustrates a schematic showing the fluidics subsystem 110 and the hand piece 118. The fluidics subsystem 110 includes an irrigation system 300 and an aspiration system 302, each in communication with the hand piece 118. The irrigation system 300 includes an irrigation source 304 as a sterile solution reservoir, an irrigation valve 306 that regulates flow from the reservoir to the surgical site, a flexible irrigation tubing 308, an irrigation path 310 in the hand piece 118, and a sleeve 312 that may be considered a component of the hand piece 118.

The irrigation system 300 extends between the sterile solution reservoir 304 and the hand piece 118, and carries fluid to the surgical site (labeled in FIG. 3 as an eye). In one example, the sterile fluid is a saline fluid, however, other fluids may be used. The flexible irrigation tubing 308 may be formed in part of the flexible tubing 112 in FIG. 2. In some embodiments, the irrigation tubing 308 is formed of multiple segments, with some segments being rigid and others being flexible. Also, in some embodiments, at least a portion of the irrigation system 300 is formed in a cassette 314 that cooperates with the console 100 in FIG. 1 to provide fluid communication between the sterile solution reservoir 304 and the patient's eye. As indicated above, in some embodiments, the irrigation sleeve 312 is disposed about the cutting needle to provide irrigating fluid flow to the eye during the surgical procedure.

In some embodiments, the aspiration system 302 includes an aspiration path 316 in the hand piece 118, a small bore flexible aspiration tubing 318, a pressure sensor 320, a pump 322, a vent valve 324, a drain line reservoir 326, and a drain reservoir 328. A hand piece connector 330 connects the aspiration path 316 in the hand piece 118 to the small bore flexible aspiration tubing 318. A cassette connector 332 connects the flexible aspiration tubing 318 to the cassette aspiration line in the cassette 314. As can be seen, the aspiration system 302 extends from the surgical site (eye) to the drain reservoir 328. It carries away fluid used to flush the eye as well as any emulsified particles. As described above with reference to the flexible irrigation tubing 308, at least a portion of the small bore flexible aspiration tubing 318 may be formed of the flexible tubing 112. In some embodiments, the aspiration system 302 is formed of multiple segments, with some segments being rigid and others being flexible. Also, in some embodiments, at least a portion of the aspiration system 302 is formed in the cassette 314 that cooperates with the console 100 in FIG. 1 to provide fluid communication between the hand piece 118 and the drain reservoir 328. It should be apparent that the drain reservoir 328 may in fact be a drain instead of a self-contained reservoir. As indicated above, in some embodiments, the aspiration system 302, including the aspiration fluid path 316, is in fluid communication with the bore of the cutting tip (labeled 334 in FIG. 3) of the hand piece 118 and is used to aspirate fluid and emulsified particles through the needle bore and into the aspiration system 302 during the surgical procedure.

For ease of explanation, the flexible tubing 112 will be described first, followed by a description of additional components of the aspiration system 302.

Figure 4:
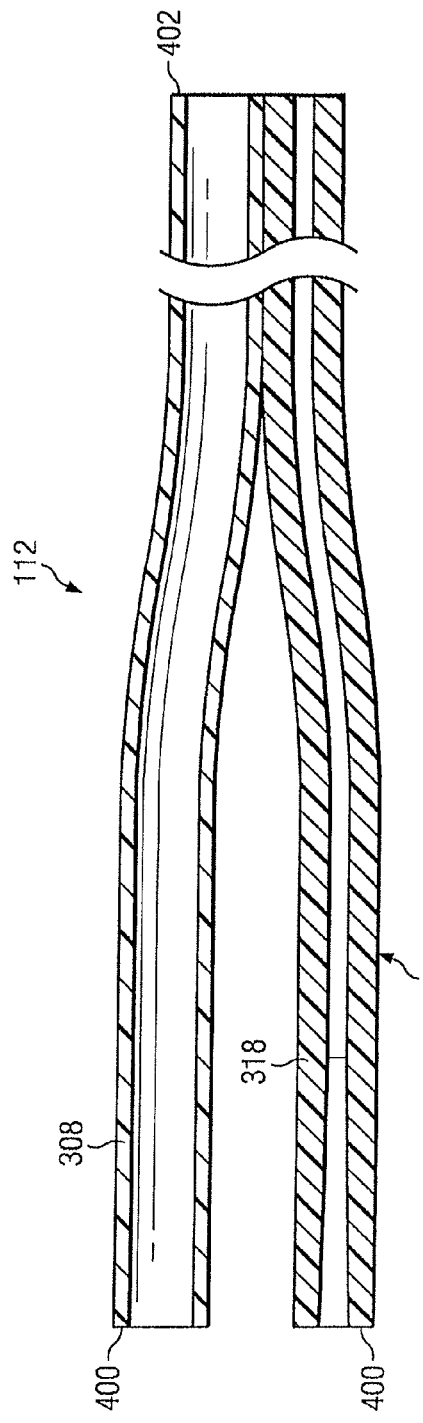
FIG. 4 is an illustration of a cross-sectional view of flexible tubing usable with the fluidics subsystem in FIG. 3, according to an embodiment.

FIG. 4 shows an exemplary embodiment of the flexible tubing 112 in cross-section, comprised of the irrigation flexible tubing 308 and the small bore aspiration flexible tubing 318. As indicated above and in FIG. 3, the irrigation flexible tubing 308 connects the hand piece 118 to the irrigation line in the cassette 314, and the small bore aspiration flexible tubing 318 connects the hand piece 118 to the aspiration line in the cassette 314.

The flexible tubing 112 extends from a proximal end 400 configured to connect to the cassette 314 to a distal end 402 configured to connect to the hand piece 118 through the hand piece connector 330. In this embodiment, the irrigation and aspiration flexible tubings 308, 318 are connected at the distal end 402, forming a dual lumen distal end. This facilitates connection to the hand piece 118, simplifying assembly of the surgical components prior to a surgery. In other embodiments however, the irrigation and aspiration tubing 308, 318 are independent tubes entirely, and in yet other embodiments, the irrigation and aspiration tubing 308, 318 are entirely connected as dual lumen systems. Other arrangements are contemplated, including arrangements where the flexible tubing 112 is formed as dual lumen system between the distal and proximal ends, but the proximal and distal ends are each split into two independent lines.

As is apparent in FIG. 4, the irrigation flexible tubing 308 has an inner diameter of a larger, first size, and the small bore aspiration flexible tubing 318 has an inner diameter of a smaller, second size. In some examples, the inner diameter of the irrigation flexible tubing 308 is around 0.25 inches, although both smaller and larger dimensions are contemplated.

The inner diameter of the small bore aspiration flexible tubing 318 is about 0.050 inches or less (other diameters are also contemplated). In the example shown, the small bore flexible tubing 318 has an average inner diameter in the range of about 0.040-0.050 inch, and in some embodiments, about 0.045 inch (other diameters are also contemplated). Accordingly, the inner diameter is about 27% ((0.062−0.045 inch)/ 0.062 inch) smaller than the aspiration tubes used in some conventional systems. In other examples, the average inner diameter is in the range of 0.035-0.045 inch (other diameters are also contemplated). The inner diameter is substantially consistent across the axial length of the aspiration flexible tubing 318, without orifices or bottle-necks that would increase the tubing resistance. Further, the walls are substantially smooth, such that the flow through the tubing is substantially laminar, without disrupting barriers.

The inner diameter of the aspiration flexible tubing 318 may be considerably smaller than the inner diameter of conventional aspiration tubes used in phacoemulsification systems. Because of the challenges surrounding the use of smaller aspiration tubing, conventional systems use tubing with an inner diameter within the range of, for example, about 0.060 or larger, typically about 0.062 inches. Here however, small bore tubing, that is, tubing with an inner diameter of about 0.050 inch or less, is used to control the levels of occlusion surge to a degree that may not be obtainable using the conventional flexible larger tubing.

The smaller diameter of the small bore aspiration tubing 318 provides a higher tube resistance than that of aspiration systems using larger diameter aspiration lines. As discussed above, this higher tube resistance decreases the levels of occlusion surge occurring when the tip 334 becomes occluded during a surgical procedure, providing more control to a surgeon. In addition, because the small bore aspiration flexible tubing 318 has a smaller surface area on the inner diameter, and has substantially the same outer diameter as the irrigation line, the small bore aspiration flexible tubing 318 may be less compliant to radial compression from vacuum surges than larger bore aspiration tubes. This reduced compliance may result in smaller levels of occlusion surge as explained above.

The aspiration system 302 is also configured to reduce the propensity for clogging at the junction of the small bore aspiration flexible tubing 318 and the aspiration path 316 and at the junction of the small bore aspiration flexible tubing 318 and the cassette 314. In some embodiments, it does this by cooperating with the connectors 330, 332 to provide a smooth transition from the hand piece 118 and to the cassette 314. For example, the small bore aspiration flexible tubing 318 has a flared inner diameter at the regions of the distal end 402 and the proximal end 400. For ease of discussion, this flared inner diameter will be discussed only with reference to a proximal end portion 404 at the small bore tubing's proximal end 400. It is understood that the distal end 402 may include the same or similar structure. This proximal end portion 404 will be described with reference to FIG. 5.

Figure 5:
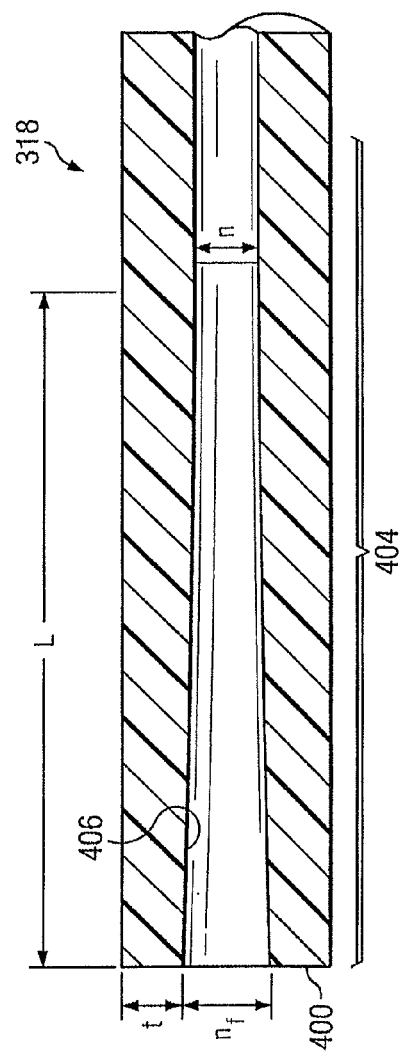
FIG. 5 is an illustration of a cross-sectional view of an end portion of the flexible tubing of FIG. 4, according to an embodiment.

Turning to FIG. 5, in some embodiments, the proximal end portion 404 includes a flared inner diameter surface 406 increasing from the nominal diameter n of the small bore aspiration tubing 318 to a flared diameter $n_f$ at the proximal end 400. In some examples, the nominal diameter n is within the range of about 0.040-0.050 inch, and the flared diameter $n_f$ is within the range of about 0.060-0.070 inch (other diameters are also contemplated). In one example, the nominal diameter is about 0.045 inch. In other examples, the nominal diameter is in the range of 0.035-0.045 inch. This flared inner diameter enables the small bore aspiration tubing 318 to connect with female connectors while maintaining a low propensity for clogging. In the example shown, the flared diameter increases linearly from the nominal diameter 11 for a distance L along the aspiration tubing 318 to the end 400, to the nominal flared diameter nf. Although not readily apparent from FIG. 5, the outer diameter of the aspiration tubing 318 also decreases over the length L. In one example, the nominal outer diameter of the tubing 318 is about 0.155 inch, and the outer diameter decreases over the length L to a diameter of 0.152 at the end 400 (other diameters are also contemplated). These features result in a wall thickness t at the end 400 that is narrower than the wall thickness away from the tubing ends. The purpose of these diameter changes is explained further below with reference to FIGS. 6-9.

Figure 8:
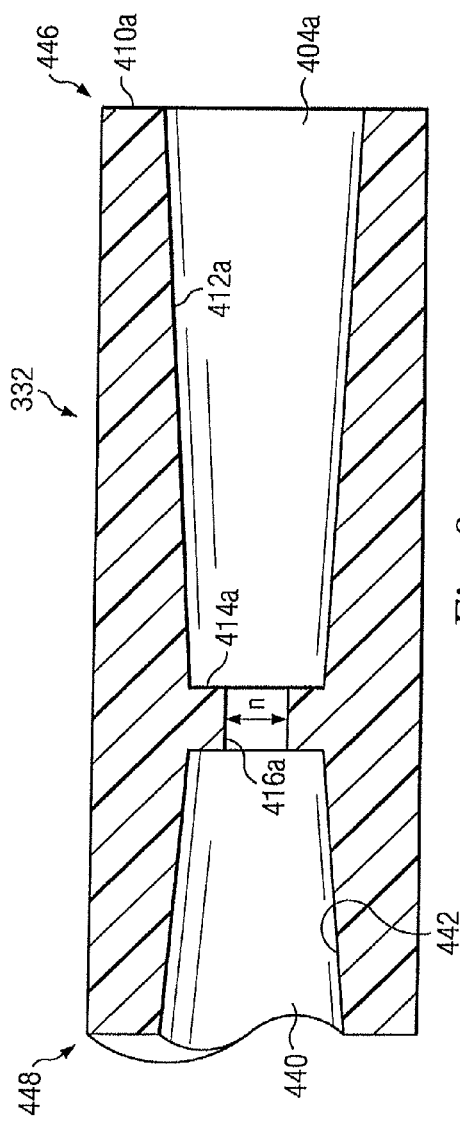
FIG. 8 is an illustration of a cross-sectional view of another connector usable to connect the flexible tubing in FIGS. 4 and 5 to additional aspiration components of the fluidics system in FIG. 3 according to one aspect of the present disclosure.
Figure 9:
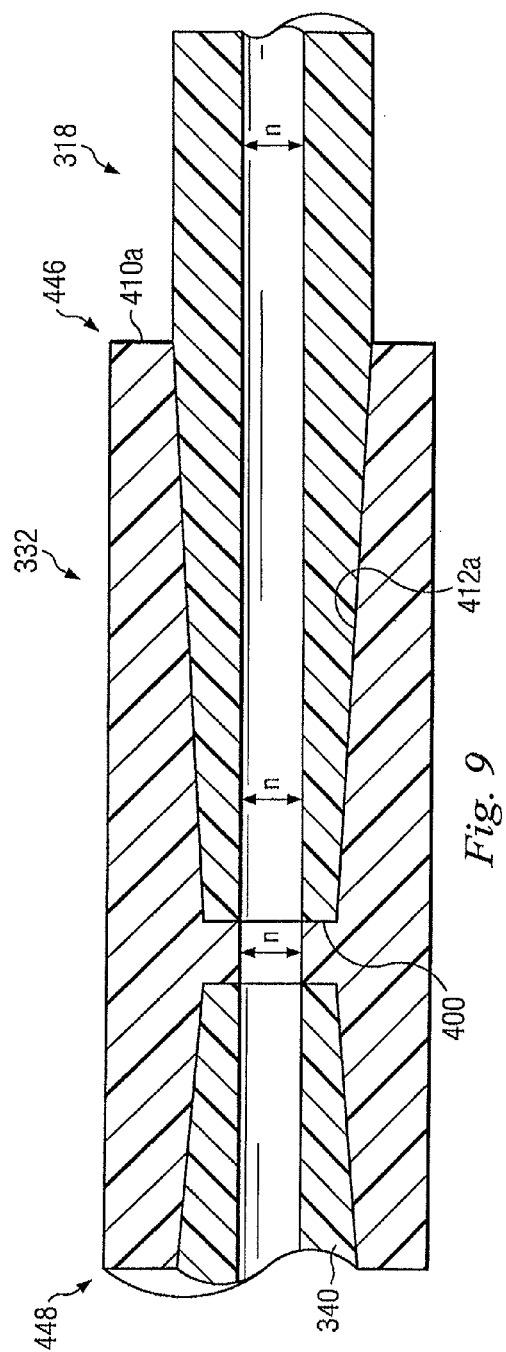
FIG. 9 is an illustration of a cross-sectional view of the connector of FIG. 8 with the end portion of FIG. 5 of the flexible tubing according to one aspect of the present disclosure.

FIGS. 6 and 7 show the connector 330 that connects the small bore aspiration tubing 318 to the aspiration path 316 in the hand piece 118. FIGS. 8 and 9 show the connector 332 that connects the small bore aspiration tubing 318 to the fluid path in the cassette 314.

The aspiration fluid path 316 (FIG. 3) within the hand piece 118 typically comprises a rigid tube configured to convey the aspiration fluid and emulsified tissue from the ultrasonic tip 334 in the surgical site to the small bore flexible aspiration tubing 318. In this embodiment, the aspiration fluid path 316 is a substantially straight-line pathway from the tip 334 to the small bore flexible aspiration tubing 318. In a conventional system, the aspiration path of the hand piece terminates in a connector such as a male luer and the aspiration tubing terminates in a mating connector such as a female luer. This typically results in an expanded fluid path diameter where the two connectors come together. This expanded diameter can be an area where clogging occurs because particulates may reorient themselves in this expanded area. The connector 330 however, helps overcome these disadvantages.

As can be seen in FIG. 6, in some embodiments, the connector 330 includes a first end 400 and a second end 402. A first bore 404 and a second bore 406 are respectively formed in the first and second ends 400, 402. The first bore 404 includes an open receiving bore end 410, a conical inner bore surface 412, a bore end 414, and a neck 416. In this embodiment, the neck 416 has a diameter substantially matching that of the nominal diameter n of the small bore aspiration tubing 318. The open receiving bore end 410 has an inner diameter substantially matching the nominal outer diameter of the small bore aspiration tubing 318. The depth of the first bore 404 may substantially match that of the of the distance L of the aspiration tubing in FIG. 5. Likewise, at the bore end 414, the distance between the inner bore surface 412 and the neck 416 may be substantially equal to the wall thickness t of the aspiration tubing 118 at its tapered end.

In some embodiments, the second bore 406 includes an open receiving bore end 420, an inner bore surface 422, and a bell-shaped curving bore surface 424 leading to the neck 416. The second bore 406 is sized to receive an end of the aspiration path 316 through the hand piece 118. Accordingly, the bore 406 has a diameter sized to receive the end of the aspiration path 316.

Since in some embodiments, the aspiration path 316 is sized in the range of about 0.062 inch or larger, the flow from the aspiration path 316 is funneled as a nozzle into the neck 416. The bore 406 is particularly shaped with the bell-shaped curve to avoid clogging, while still carrying the fluid and emulsified particles through the neck 416. Accordingly, to minimize the propensity for clogging, the length of the bore 406 at its largest diameter is minimized to facilitate particles remaining oriented along the flow lines. In addition, instead of having a stepped or squared end as conventional connectors do, the connector 330 has a bell-shaped, curved surface 424 that provides an uninterrupted smooth transition from a larger diameter of the bore end 420 down to the diameter of the neck 416, which, as explained above, substantially matches the nominal diameter n of the small bore aspiration tubing 318. The bell-shape helps by narrowing the length required for the transition from the large diameter to the neck while still providing a smooth flow path. This may provide a better flow than a long linearly tapering path. Thus, the tubing connector 330 helps the small bore aspiration system operate effectively to control occlusion surge.

FIG. 7 shows the connector 330 attached to the aspiration path 316 in the hand piece 118 and to a distal end 402 of the small bore aspiration tubing 318. The conical inner bore surface 412 of the connector 330 is particularly designed to cooperate with the flared end of the small bore aspiration tubing 318 as shown in FIG. 7 in order to maintain the nominal diameter n, even when the end 402 is compressively deformed to fit within the female connector 330. As indicated above, the distal end 402 of the tubing 318 also includes a flared end. Conventional, non-flared tubes have an inner diameter that may radially deform or collapse to a diameter less than the nominal diameter n if used in female connectors, potentially creating a bottle-neck with increased propensity for clogging. However the connector 330 is particularly designed to receive the flexible tubing end 402, and deform the end portion in a manner not overly restricting flow. In this embodiment, it may deform the end portion only to the extent that either maintains the nominal diameter n or still results in a diameter greater than the diameter n. The taper on the outer diameter discussed with reference to FIG. 5 enables easier insertion into the connector 330.

FIG. 8 shows the connector 332 that connects the small bore aspiration tubing 318 to the fluid path in the cassette 314. As can be seen, the connector 332 includes a first end 446 and a second end 448. The first end 446 is substantially equivalent to the first end 400 in the connector 330, and the first end 446 is particularly structured to cooperate with the small bore flexible aspiration tubing 318 in order to maintain the nominal diameter n, even when the end is deformed to fit within the female connector 332. Since the first end 446 is structurally similar to the first end 400 of the connector 330 in FIG. 6, it is labeled with similar reference numerals. The first end 446 includes a first bore 404a with an open receiving bore end 410a, a conical inner bore surface 412a, a bore end 414a, and a neck 416a. The neck 416a has a diameter matching that of the nominal diameter n of the small bore aspiration tubing 318. The description above of the first end 400 in FIG. 6 is equally applicable to the first end 446, and is not repeated here.

The second end 448 of the connector 332 is configured to interface with the cassette 314. In the embodiment shown, the cassette 314 is a conventional cassette and includes a fluid pathway connectable with the connector 332. The pathway 332 has an inner diameter sized greater than the inner diameter of the small bore aspiration tubing 318. Accordingly, the connector 332 is particularly configured to receive the fluid passage from the cassette 314. The second end includes an open receiving end 440, a conical surface 442, and a bore end 444 leading to the neck 416a.

FIG. 9 shows the connector 332 connected to the proximal end 400 of the small bore aspiration tubing 318 and the fluid path 340 from the cassette 314. Similar to the bore 404 in the connector 330, the open receiving bore end 410a has an inner diameter substantially matching the nominal outer diameter of the flexible aspiration tubing 318. The depth of the first bore 404a may substantially match that of the distance L of the aspiration tubing 318 in FIG. 5. Likewise, at the bore end 414a, the distance between the inner bore surface 412 and the neck may be substantially equal to the wall thickness t of the aspiration tubing 318 at its tapered end.

Because the connector 332 is particularly designed to receive the aspiration tubing end, and deform the end portion in a manner not overly restricting flow, the propensity for clogs is reduced, resulting in a smoother, more laminar transition through the connector than conventional aspiration systems. This helps make the use of a small bore aspiration tubing to control occlusion surge more effective, without the drawbacks of clogging. Further, as described above, the taper on the outer diameter of the small bore aspiration tubing 318 discussed with reference to FIG. 5 enables easier insertion into the connector 332.

The pump 322 of the aspiration system 302 is associated with the cassette 314 and is configured to create a vacuum in the aspiration system 302 to draw fluid and emulsified particles from the surgical site. The high fluid resistance associated with the small bore aspiration tubing 118 may result in greatly reduced efficiency for most peristaltic pumps. This fluid resistance, while beneficial for reducing the levels of occlusion surge, can also result in the inability to generate desire levels of aspiration flow rate (typically up to 60 cc/min) or can require a need to run the pump at a very high rate of speed resulting in objectionable acoustic noise. Accordingly, because of the small bore of the aspiration tubing 318, a conventional pump may not achieve the vacuum required for suitable flow at the surgical tip. The pump 322, therefore, may be a high-output pump capable of creating the vacuum necessary to achieve suitable flow rates through the small bore aspiration tubing 318. In some examples, the pump 322 is a bidirectional peristaltic pump. In some embodiments, the pump 322 represents multiple pumps that operate in parallel. In some aspects, the pump is as described in U.S. patent application Ser. No. 12/755,539, filed Apr. 7, 2010, which is incorporated herein by reference.

Accordingly, the aspiration system 302 employs small bore aspiration lines, with a diameter of 0.050 inches or less (other diameters are also contemplated) to achieve lower levels of occlusion surge than currently known systems under similar conditions. In some embodiments, the small bore aspiration tubing 318 inner diameter is within the range of 0.040-0.050, and in some examples, around a nominal diameter of about 0.045 inch. In other examples, the average inner diameter is in the range of 0.035-0.045 inch (other diameters are also contemplated).

The small bore lines provide increased fluid resistance that dampens or reduces the levels of occlusion surge in the aspiration line. These lines accomplish this by introducing a greater level of wall resistance than larger bore fluid paths and by being less compliant when subjected to high vacuum levels within the tubing. At the same time, the aspiration system maintains suitable flow rates with reduced clogging. This decreases the level of occlusion surges and provides more control during surgical procedures.

In one embodiment of the aspiration system 302, the aspiration fluid path 316 in the hand piece 118 has a small bore inner diameter, less than about 0.050 inches (other diameters are also contemplated), and in some embodiments, matching one or both of the inner diameter of the small bore aspiration tubing 318 and the inner diameter of the ultrasonic tip 334.

Aspiration fluid paths within a conventional hand piece are larger bore tubes having an inner diameter typically sized greater than 0.060 inches. This may be considerably larger than a conventional lumen size of the ultrasonic tip (typically 0.045 inches or less). As such, in conventional systems, emulsified particles passing through the tip may have a non-symmetrical shape and may be oriented longitudinally to the direction of flow. As the particles pass from the tip into the aspiration path in a conventional hand piece, the particles have an opportunity to reorient. These reoriented particles have a greater propensity to clog the aspiration system further down line.

In this embodiment, however, the aspiration fluid path 316 has a small bore inner diameter, less than about 0.050 inches, sized to cooperate with the lumen diameter of the ultrasonic tip and the small bore aspiration tubing 318. In some embodiments, the inner diameter of the aspiration fluid path 316 is within the range of 0.040-0.050, and in some examples, around a nominal diameter of about 0.045 inch. In other examples, the average inner diameter is in the range of 0.035-0.045 inch (other diameters are also contemplated). In other embodiments, the aspiration fluid path 316 lumen is sized to match that of the ultrasonic tip lumen (i.e., the needle bore).

In some embodiments, the size ratio between the inner diameter of the small bore aspiration tubing 318 and the inner diameter of the ultrasonic tip may be minimized. For example, a size ratio between the aspiration tubing 318 inner diameter and the needle bore inner diameter may be less than about 1.3. In one embodiment, the needle bore inner diameter may be approximately 0.0354 inches and the aspiration tubing 318 inner diameter may be approximately 0.045 inches for a size ratio between the aspiration tubing 318 inner diameter and the needle bore inner diameter of about 1.27 (i.e., 0.045 inches/0.0354 inches). Other size ratios are also contemplated (e.g., 1.5).

Because its inner diameter size may be less than that of conventional systems, the aspiration path 316 in the aspiration system 302 creates a higher tube resistance. As discussed above, this higher tube resistance decreases the levels of occlusion surge occurring when the tip 334 becomes occluded during a surgical procedure.

In some embodiments, the inner diameter of the small bore aspiration tubing 318 may substantially match the inner diameter of the aspiration fluid path 316 in the hand piece. For example, a size ratio between the hand piece aspiration fluid path inner diameter and the needle bore inner diameter may also be about 1.3 (other size ratios are also contemplated). If the inner diameter of the aspiration fluid path 316 of the hand piece is the same as or less than that of the flexible aspiration tubing 318, then propensity for clogging can be further reduced. In this way, particles aligned longitudinally with the pathway stay longitudinally aligned, with less opportunity to reorient in a position that may result in clogging or occlusion of the aspiration system 302. In such embodiments, the tapering that occurs in the connector 330 may be replaced with a flat end that abuts the end of the aspiration path 316 and has a neck with a diameter substantially matching the nominal diameter of the aspiration path 316 and the small bore aspiration tubing 318.

In use, the flexible tubing 112 is attached to the hand piece 118 prior to conducting the surgery. Irrigation fluid is directed to the surgical site through the irrigation system 300. The aspiration system 302 conveys fluid from the surgical site to the waste reservoir or drain 328. This is accomplished by vacuuming fluid and emulsified tissue from the surgical site with the phacoemulsification needle tip 334. The fluid passes to the aspiration path 316 in the hand piece 118. The fluid then flows through the connector 330 into the small bore flexible aspiration tubing 318. The connector 330 is configured to minimize clogging by creating minimal turbulence and by minimizing transitions from diameters larger than the diameter of the small bore flexible aspiration tubing 318. The fluid flows though the small bore flexible aspiration tubing 318 to the cassette 314, and through the connector 332 at the cassette. As described above, the diameter of the inner flexible tubing is substantially maintained at its nominal size, even through the female connector 334 due to its flared configuration. The flow continues to the pump 322, which may be a high-output, bidirectional peristaltic pump.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. An assembly for a phacoemulsification surgical system, comprising:
    an irrigation system configured to provide irrigating fluid to a phacoemulsification hand piece to irrigate a surgical site; and
    an aspiration system arranged to aspirate aspirating fluid from the surgical site, comprising:
        a flexible small bore aspiration tubing configured to be in fluid communication with an aspiration path of the phacoemulsification hand piece, the small bore aspiration tubing having a nominal inner diameter smaller than about 0.050 inch to reduce levels of occlusion surge within the surgical system; and
        a peristaltic pump in communication with the small bore aspiration tubing operable to create a flow through the small bore aspiration tubing;
        wherein the small bore aspiration tubing comprises a flared portion on the inner diameter of at least one end, wherein when in an unloaded condition, the flared portion has an inner diameter larger than the nominal inner diameter of the small bore aspiration tubing;
        a connector configured to receive at least a portion of the flared portion of the small bore aspiration tubing, the connector being sized to apply radial compression on the flared portion when the flared portion is inserted in the connector such that when the small bore aspiration tubing is disposed within the connector, the inner diameter of the flared portion is about the same diameter as the nominal diameter of the small bore aspiration tubing.

2. The assembly of claim 1, comprising a connector disposed between the aspiration path in the hand piece and the small bore aspiration tubing, the connector comprising a neck for passage of the aspiration fluid, the neck having a diameter substantially matching the nominal inner diameter of the small bore aspiration tubing.

3. The assembly of claim 1, wherein the pump comprises a high output parallel operating pump operable to create a flow of about 60 cc/min. through the small bore aspiration tubing.

4. The assembly of claim 1, wherein the small bore aspiration tubing has an inner diameter within a range of about 0.035-0.050 inch.

5. The assembly of claim 4, wherein the small bore aspiration tubing has an inner diameter sized about 0.045 inch.

6. The assembly of claim 1, further comprising a phacoemulsification hand piece configured to deliver the irrigating fluid to the surgical site, the phacoemulsification hand piece comprising an ultrasonic tip having a lumen sized and configured to aspirate the aspirating fluid from the surgical site;
    wherein the phacoemulsification hand piece comprises an aspiration path, the aspiration path extending from the ultrasonic tip and being arranged and configured to permit flow of the aspirating fluid through the hand piece;
    wherein the aspiration path within the hand piece comprises an inner diameter matching the inner diameter of the lumen of the ultrasonic tip.

7. An assembly for a phacoemulsification surgical system, comprising:
    an irrigation system configured to provide irrigating fluid to a phacoemulsification hand piece to irrigate a surgical site; and
    an aspiration system arranged to aspirate aspirating fluid from the surgical site, comprising:
        a flexible small bore aspiration tubing configured to be in fluid communication with an aspiration path of the phacoemulsification hand piece, the small bore aspiration tubing having a nominal inner diameter smaller than about 0.050 inch to reduce levels of occlusion surge within the surgical system; and
        a peristaltic pump in communication with the small bore aspiration tubing operable to create a flow through the small bore aspiration tubing;
        wherein the small bore aspiration tubing comprises a flared portion on the inner diameter of at least one end, wherein when in an unloaded condition, the flared portion has an inner diameter larger than the nominal inner diameter of the small bore aspiration tubing;
    a connector disposed between the aspiration path in the hand piece and the small bore aspiration tubing, the connector comprising a neck for passage of the aspiration fluid, the neck having a diameter substantially matching the nominal inner diameter of the small bore aspiration tubing;

wherein the connector comprises two female ends sized respectively to receive the aspiration path and the small bore aspiration tubing, the connector having a smooth transition from a largest inner diameter of the connector down to the neck diameter.

8. The assembly of claim 7, wherein when in an unloaded condition, the flared portion has an inner diameter larger than the nominal inner diameter of the small bore aspiration tubing, the assembly further comprising:

a cassette associated with the pump; and a second connector disposed between the small bore aspiration tubing and the cassette, the second connector configured to receive at least a portion of the flared portion of the small bore aspiration tubing and to apply radial compression on the flared portion when the flared portion is inserted in the connector such that when the small bore aspiration tubing is disposed within the connector, the inner diameter of the flared portion is about the same diameter as the nominal diameter of the small bore aspiration tubing.

9. A small bore aspiration system arranged to receive aspiration fluid from an ultrasonic tip used in a phacoemulsification surgical assembly, comprising:

an aspiration path within an phacoemulsification hand piece, the aspiration path extending from the ultrasonic tip and being arranged and configured to permit flow of the aspiration fluid through the hand piece;

a flexible small bore aspiration tubing in fluid communication with the aspiration path, the small bore aspiration tubing having a nominal inner diameter smaller than about 0.050 inch to reduce levels of occlusion surge within the surgical assembly, the inner diameter being substantially consistent through the small bore aspiration tubing; and a high-output, peristaltic pump in communication with the small bore aspiration tubing;

a connector configured to receive at least a portion of the flared portion of the small bore aspiration tubing, the connector being sized to apply radial compression on the flared portion when the flared portion is inserted in the connector such that when the small bore aspiration tubing is disposed within the connector, the inner diameter of the flared portion is about the same diameter as the nominal diameter of the small bore aspiration tubing;

wherein the small bore aspiration tubing comprises a flared portion on the inner diameter of at least one end, wherein when in an unloaded condition, the flared portion has an inner diameter larger than the nominal inner diameter of the small bore aspiration tubing.

10. The assembly of claim 9, comprising a connector disposed between the aspiration path in the hand piece and the small bore aspiration tubing, the connector comprising a neck for passage of the aspiration fluid, the neck having a diameter substantially matching the nominal inner diameter of the small bore aspiration tubing.

11. The assembly of claim 9, wherein the small bore aspiration tubing has an inner diameter within a range of about 0.035-0.050 inch.

12. The assembly of claim 11, wherein the small bore aspiration tubing has an inner diameter sized about 0.045 inch.

13. A small bore aspiration system arranged to receive aspiration fluid from an ultrasonic tip used in a phacoemulsification surgical assembly, comprising:

an aspiration path within an phacoemulsification hand piece, the aspiration path extending from the ultrasonic tip and being arranged and configured to permit flow of the aspiration fluid through the hand piece;

a flexible small bore aspiration tubing in fluid communication with the aspiration path, the small bore aspiration tubing having a nominal inner diameter smaller than about 0.050 inch to reduce levels of occlusion surge within the surgical assembly, the inner diameter being substantially consistent through the small bore aspiration tubing; and a high-output, peristaltic pump in communication with the small bore aspiration tubing;

wherein the small bore aspiration tubing comprises a flared portion on the inner diameter of at least one end, wherein when in an unloaded condition, the flared portion has an inner diameter larger than the nominal inner diameter of the small bore aspiration tubing;

a connector disposed between the aspiration path in the hand piece and the small bore aspiration tubing, the connector comprising a neck for passage of the aspiration fluid, the neck having a diameter substantially matching the nominal inner diameter of the small bore aspiration tubing;

wherein when in an unloaded condition, the flared portion has an inner diameter larger than the nominal inner diameter of the small bore aspiration tubing, the assembly further comprising:

a cassette associated with the pump; and a second connector disposed between the small bore aspiration tubing and the cassette, the second connector configured to receive at least a portion of the flared portion of the small bore aspiration tubing and to apply radial compression on the flared portion when the flared portion is inserted in the connector such that when the small bore aspiration tubing is disposed within the connector, the inner diameter of the flared portion is about the same diameter as the nominal diameter of the small bore aspiration tubing.

14. A method for aspirating a surgical site with an aspiration system of a phacoemulsification surgical system, comprising:

creating a vacuum in an aspiration system of a phacoemulsification system;

directing fluid through a needle of a phacoemulsification hand piece;

directing fluid through an aspiration passage within the hand piece;

directing fluid through a small bore flexible aspiration tubing extending from the hand piece to a fluid cassette, the small bore flexible aspiration tubing having a substantially consistent nominal diameter across its length, the nominal diameter being less than about 0.050 inch, wherein the size ratio between the small bore flexible aspiration tubing inner diameter and the needle bore inner diameter is less than about 1.3; and directing fluid into a cassette and a pump configured to create a vacuum in the aspiration system;

wherein directing fluid into a cassette includes directing the fluid through a connector and a radially deformed portion of the flexible tubing, the radial deformed portion of the flexible tubing having an inner diameter substantially consistent with the inner diameter of the flexible tubing.

15. The method of claim 14, wherein directing fluid through an aspiration passage within the hand piece comprises directing fluid through the aspiration passage having a size ratio between the hand piece aspiration fluid path inner diameter and the needle bore inner diameter of less than about 1.3.

* * * * *